US008206731B2

(12) United States Patent
Harichian et al.

(10) Patent No.: US 8,206,731 B2
(45) Date of Patent: Jun. 26, 2012

(54) SELF-TANNING EFFECTS

(75) Inventors: Bijan Harichian, Brookfield, CT (US); Anthony John Weir, Westport, CT (US); Michael Charles Cheney, Trumbull, CT (US); Zhi-xing Jiang, Southbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 952 days.

(21) Appl. No.: 12/194,674

(22) Filed: Aug. 20, 2008

(65) Prior Publication Data
US 2009/0155322 A1 Jun. 18, 2009

Related U.S. Application Data

(60) Provisional application No. 61/012,985, filed on Dec. 12, 2007.

(51) Int. Cl.
*A61K 8/02* (2006.01)
*A61K 8/00* (2006.01)
*A61K 8/18* (2006.01)
*A61Q 17/04* (2006.01)

(52) U.S. Cl. .......................................... 424/401; 424/59

(58) Field of Classification Search .................... 424/401
See application file for complete search history.

(56) References Cited

U.S. PATENT DOCUMENTS

| | | | |
|---|---|---|---|
| 6,024,968 A * | 2/2000 | Suess et al. .................... 424/401 |
| 6,482,397 B1 * | 11/2002 | Scott et al. ....................... 424/59 |
| 2003/0133887 A1 | 7/2003 | Forestier et al. |
| 2007/0017921 A1 | 1/2007 | Carmona |
| 2007/0048238 A1 | 3/2007 | Sandewicz et al. |
| 2007/0104951 A1 | 5/2007 | Ito |
| 2007/0167338 A1 * | 7/2007 | McHugh et al. ............. 510/130 |
| 2007/0218024 A1 | 9/2007 | Zamyatin et al. |
| 2007/0292373 A1 | 12/2007 | Russ et al. |
| 2008/0081057 A1 | 4/2008 | Chevalier |

FOREIGN PATENT DOCUMENTS

| | | |
|---|---|---|
| DE | 102007059679 A1 * | 9/2008 |
| EP | 1 911 437 A1 | 8/2005 |
| EP | 1 908 452 A1 | 8/2007 |
| WO | WO9951197 | 10/1999 |
| WO | WO0135933 A2 | 5/2001 |
| WO | 2007/017921 A1 | 2/2007 |
| WO | WO2007023495 A2 | 3/2007 |

OTHER PUBLICATIONS

PCT International Search Report—PCT/EP2008/061628.
PCT Written Opinion—PCT/E-2008/061628.
Co-Pending Appln.—Harichian et al.—U.S. Appl. No. 61/012,973, filed Dec. 12, 2007—Entitled: Compositions With Encapsulated Coloring Agents and Method to Impart a Healthy Skin Appearance.
Co-Pending Appln.—Huang et al.—U.S. Appl. No. 12/111,993, filed Apr. 30, 2008—Entitled: Cosmetic Compositions and Method Which Impart a Healthy Appearance to Skin.
Material Safety Data Sheet, Tagra Biotechnologies Ltd., Feb. 2006.
Reisch, Ushering Cosmetics to the Right Spots, Chemical & Engineering News, May 14, 2007, vol. 85, No. 20, 15-21.

* cited by examiner

*Primary Examiner* — Sreeni Padmanabhan
*Assistant Examiner* — Layla Soroush
(74) *Attorney, Agent, or Firm* — Milton L. Honig

(57) ABSTRACT

A cosmetic composition and method is herein described for sunless tanning to impart a glow/shiny effect on skin. The composition includes a sunless tanning agent and coated beads incorporating tan colored pigment. A colorant which imparts a color other than tan to the beads is distributed within the coating. The cosmetic composition provides to the skin an immediate tan via the disintegrated beads. Sunless tanning agent acts more slowly and eventually will replace the pigment effect. The coating with colorant prevents the formula undesirably from appearing tan. Instead a color such as white renders the formula more aesthetically pleasing and more in line with the visuals paradigm of a moisturizer rather than a foundation.

6 Claims, No Drawings

SELF-TANNING EFFECTS

BACKGROUND OF THE INVENTION

1. Fiend of the Invention

The invention concerns a cosmetic product for rapidly delivering a sunless tanning or a glow effect upon skin.

2. The Related Art

Sunless tanning agents are formulated into two types of cosmetic products. Of these, the most traditional is the self-tanning lotion. The imparted benefit is to achieve a skin coloration equivalent to that from basking in the sun. More recently, a second product category has arrived. Therein a sunless tanning agent in small amounts is added to a typical moisturizing lotion. A "glow or shine" is thereby imparted. Glow or shine is a major factor in the appearance of healthy looking skin.

Most prominent among the sunless tanning agents is dihydroxyacetone ("DHA" which is also chemically known as 1,3-dihydroxy-2-propanone). DHA is believed to exert its effect through interactions between its hydroxyl groups and the amino groups of amino acids and peptides naturally occurring in the hydrolipid pellicle and first layers of the stratum corneum of the skin. These so-called Maillard reactions are believed (see, e.g., Bobin et al., J. Soc. Cosmet. Chem. 35: 255 (1984)) to lead to formation of brown pigments in the skin, thereby giving it an appearance similar to that of a naturally obtained tan.

WO 2007/017921 A1 (Shiseido Company, Ltd.) reports on a self-tanning cosmetic with dihydroxyacetone and inorganic pigment powder. The powder is prepared by subjecting an inorganic pigment to a surface coating of silica followed by a hydrophobic treatment. The finished cosmetic is said to be free of any color change and of the evolution of an offensive odor, has high storage stability and can establish both the desired performance immediately and after application to the skin owing to the pigment and a long lasting tanning effect owing to dihydroxyacetone.

Although there has been great progress in delivering effects of self-tanning, considerable further progress is needed. In particular, it would be desirable to achieve almost instantaneous glow, shine or tanning upon application to bridge the relatively long induction period of a sunless tanning agent. Further, it would be aesthetically and psychologically desirable to retain a distinction between the color of the delivering cosmetic formula and that of the eventual tan.

SUMMARY OF THE INVENTION

A cosmetic composition is provided which includes:
(i) from about 0.05 to about 15% by weight of the composition of a sunless tanning agent;
(ii) from about 0.1 to about 20% by weight of the composition of beads having an average particle size ranging from about 100 to about 3,000 micron ($\mu$m);
(iii) from about 1 to about 60% by weight of the beads of a water-insoluble pigment incorporated within a matrix of the beads, the pigment having a tan color;
(iv) from about 0.1 to about 10% by weight of the beads of a colorant held within a coating surrounding the matrix, the coating having a color other than tan; and
(v) a cosmetically acceptable carrier.

Further, a method is provided for sunless tanning or delivery of a glow/shine to human skin which includes:
(A) providing a cosmetic composition which includes:
(i) from about 0.05 to about 15% by weight of the composition of a sunless tanning agent;
(ii) from about 0.1 to about 20% by weight of the composition of beads having an average particle size ranging from about 100 to about 3,000 micron ($\mu$m);
(iii) from about 1 to about 60% by weight of the beads of a water-insoluble pigment incorporated within a matrix of the beads, the pigment having a tan color;
(iv) from about 0.1 to about 10% by weight of the beads of a colorant held within a coating surrounding the matrix, the coating having a color other than tan;
(v) a cosmetically acceptable carrier; and
(B) applying the cosmetic composition to the skin.

DETAILED DESCRIPTION OF THE INVENTION

Now it has been found that instant coloration can be applied to a skin area considered in need of a sunless tanning or glow/shiny benefit. A sunless tanning agent is one of two benefit materials in the cosmetic compositions of this invention. Although this agent provides the longer term tan benefit, it operates through chemical interaction with skin proteins in a relatively delayed manner. For this reason, a coloring amount of a water-insoluble organic or inorganic pigment is co-delivered to a consumer's body. It provides an immediate visual tan, which in time washes away.

The particular advance of the present invention is that the color of the cosmetic composition is not compromised by that of the tan pigment. The separation of color effect is achieved by incorporating a colorant into the protective polymeric coating whereby the coating renders an exterior of the bead to be colored other than tan.

Sunless tanning agents of the present invention are materials which when applied to human skin will react with amino acids of the skin so as to form pigmented species. These reactions give skin a brown appearance similar to a color obtained by exposure to sunlight. These materials may be alpha-hydroxyaldehydes and ketones, glyceraldehyde, troxerutin and related alcohol aldehydes, various indoles, imidazoles and derivatives thereof. Illustrative but not limiting are dihydroxyacetone, melanin, mahakanni (eclipta alba), methyl glyoxal, erythrulose, alloxan, 2,3-dihydroxysuccindialdehyde and mixtures thereof. More preferred is dihydroxyacetone.

Amounts of the sunless tanning agent may range from about 0.05 to about 15%, preferably from about 0.5 to about 10%, more preferably from about 0.8 to about 5%, and optimally from 1 to 2% by weight of the cosmetic composition. Of particular usefulness is a combination of dihydroxyacetone and erythrulose in a relative weight ratio of 6:1 to 1:2, preferably a ratio from 4:1 to 2:1.

A second component of the present invention is that of beads having an average particle size ranging from about 100 micron to about 3,000 micron, preferably from about 500 micron to about 1,300 micron, optimally from about 700 micron to about 900 micron. Amounts of the beads will range from about 0.1 to about 20%, preferably from about 0.5 to about 10%, and optimally from about 1 to about 8% by weight of the cosmetic composition.

Beads of this invention preferably will have matrices based on the natural polymers of cellulose and cellulose derivatives. Besides cellulose, the derivatives may include hydroxypropyl methyl cellulose, hydroxyethyl cellulose, hydroxypropyl cellulose, carboxymethyl cellulose and combinations thereof. Sugars may also be employed as a component of the matrices. These include mannitol, sorbitol, xylitol and mixtures thereof. Relative amounts of sugar to cellulose (and/or cellulose derivative) range from about 3:1 to about 1:3, preferably from about 2:1 to about 1:2 by weight of the matrix. Most preferred is a matrix of mannitol, cellulose and hydroxypropyl methyl cellulose. Amounts of hydroxypropyl methyl cellulose may range from about 0.01 to less than about 1% by weight of the matrix. Commercially this matrix in the form of beads is available from Induchem USA, Inc. under the tradename Induchem Unispheres. These beads are formed from a homogeneous spherical semi-solid matrix core consisting of mannitol, cellulose and hydroxypropyl methyl cellulose. An outer coating surrounds the matrix to insure coloring agent is prevented from leaving. This coating contains a plasticizer, polymer and a colorant.

Advantageously beads of this invention should be swellable from water when in contact with an aqueous system. Swelling may increase the volume of the beads by an amount from about 5% to about 20%, preferably from about 10% to about 18%, as measured at 25° C. over a 20 day period using 0.2% by weight of beads in water. Amount of swelling when greater than the aforedescribed range results in leakage of coloring agent from the matrix of the beads. Equally undesirable is minor or non-swelling which results in beads that do not release coloring agent during rub-in of composition onto the skin. Too much or too little swelling is therefore disadvantageous for purposes of this invention. A hydrophilic matrix functioning as a sponge with defined uptake of water is a desirable feature of this invention. Coloring agents inside the beads should be easily broken allowing them to spread during rub-in process onto skin.

A water-insoluble organic or inorganic pigment will be incorporated into the bead matrix. The pigment normally will be a combination of materials which result in a visual tan shade. Illustrative pigments include yellow iron oxide, red iron oxide, black iron oxide, brown iron oxide, titanium dioxide, carbon black, bismuth oxychloride, zinc oxide, clay, chrominium oxide and mixtures thereof. Particularly useful as pigment is a mixture of yellow iron oxide, red iron oxide, black iron oxide and titanium dioxide in mixed proportion to achieve tan shades.

Amounts of the pigment may range from about 1 to about 60%, preferably from about 5 to about 40%, optimally from about 10 to about 25% by weight of the bead. The relative weight ratio of pigment to matrix may range from about 0.4:1 to about 1:100, preferably from 0.2:1 to 1:20.

The pigment is embedded within the matrix of easily frangible beads. A polymeric coating surrounds each of the beads to prevent their premature dissolution. The beads in an aqueous medium can swell but no leakage of pigment (and thereby color) will occur because of pigment insolubility.

A colorant will be included in the coating that surrounds the beads. This will be intimately mixed with other coating components including polymer (e.g. polyacrylate) and plasticizer. Illustrative colorants in the dye grouping are FD&C Yellow 5, FD&C Yellow 6, D&C Yellow 10, D&C Red 6, D&C Red 7, D&C Red 21, D&C Red 27, D&C Red 28, D&C Red 30, D&C Red 33, D&C Red 36, D&C Red 40, D&C Green 6, carmine, D&C Blue 1, FD&C Blue 1, bromo dyes, fluoroescein dyes, and combinations thereof.

Suitable pigments for use as colorant include but are not limited to, titanium dioxide; calcium carbonate; clay; talc; barium sulfate; white carbon; chromium oxide; zinc oxide; zinc sulfide; zinc powder; metal oxide coated mica (such as titanium oxide coated mica); thin platelet-like alumina; metal oxide coated thin platelet-like alumina (such as titanium dioxide coated thin platelet-like alumina) magnesium carbonate; hydroxyapatite and mixtures thereof. Titanium dioxide in an amount to color the beads white (and cover the tan colored matrix) are most preferred.

Amounts of the colorant may range from about 0.1 to about 10%, preferably from about 0.5 to about 6%, optimally from about 1 to about 4% by weight of the beads.

As used herein, the term "cosmetic composition" is intended to describe compositions for topical application to human skin, including leave-on and wash-off products.

The term "skin" as used herein includes the skin on the face, neck, chest, back, torso, arms, axillae, hands, legs, and scalp.

As used herein, "color" is a general term intended to cover human perception of color and includes variations in lightness/darkness and/or variations in hue.

Lightness is defined in terms of the $L^*$ parameter in the $L^*-a^*-b^*$ color space, which will be discussed in more detail hereinbelow. The greater the $L^*$ value, the lighter the skin. The smaller the $L^*$ value, the darker the skin, indicating higher melanin content.

Hue is defined as the color component on a red to yellow spectrum. More specifically, hue is defined in terms of the $a^*$ and $b^*$ parameters in $L^*-a^*-b^*$ color space, as follows:

$$\text{Hue}=\tan^{-1}(b^*/a^*)$$

Usually for skin color, $a^*$ and $b^*$ are greater than zero, so the smaller the Hue value, the more red the color.

This color system is known as the Commission Internationale de l'Eclairage (CIE) $L^*a^*b^*$ color system, where:

$L^*$=Black to white (luminance) from 0 to 100 [$L^*$=0 represents Black]

$a^*$=green to red from −60 to +60

$b^*$-blue to yellow from −60 to +60 as measured by a chromameter, such as for example a hand held Minolta CM2002 chromameter.

Compositions of the present invention will also include a cosmetically acceptable carrier. Water is the most preferred carrier. Amounts of water may range from about 1 to about 99%, preferably from about 5 to about 90%, more preferably from about 35 to about 70%, optimally betveen about 40 and about 60% by weight. Ordinarily the compositions will be water and oil emulsions, most preferably of the oil-in-water variety. Indeed, in certain instances the water-n-oil emulsions should be avoided because the hydrophobicity will inhibit water dissolution of the bead matrix (i.e. cellulose) to release pigment upon rub-in of the composition onto skin.

Other cosmetically acceptable carriers may include mineral oils, silicone oils, synthetic or natural esters, fatty acids and alcohols and humectants. Amounts of these materials may range from about 0.1 to about 50%, preferably from about 0.1 to about 30%, more preferably from about 1 to about 20% by weight of the compositon.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C.

Among suitable esters are:

(1) Alkenyl or alkyl esters of fatty acids having 10 to 20 carbon atoms. Examples thereof include isopropyl palmitate, isopropyl isostearate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which soya sterol and cholesterol fatty acid esters are examples thereof.

Fatty acids having from 10 to 30 carbon atoms may be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerin. The amount of humectant may range anywhere from 0.5 to 30%, preferably between 1 and 15% by weight of the composition.

Emulsifiers may be present in cosmetic compositions of the present invention. Total concentration of the emulsifier may range from about 0.1 to about 40%, preferably from about 1 to about 20%, optimally from about 1 to about 5% by weight of the total composition. The emulsifier may be selected from the group consisting of anionic, nonionic, cationic and ampdhoteric actives. Particularly preferred nonionic surfactants are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Thickening agents may be included in compositions of the present invention. Particularly useful are the polysaccharides. Examples include starches, natural/synthetic gums and cellulosics. Representative of the starches are chemically modified starches such as aluminum starch octenylsuccinate. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are still a further class of effective thickening agent. This category includes crosslinked polyacrylates such as the Carbomers, polyacrylamides. Such as Sepigel® 305 and taurate copolymers such as Simulgel EG® and Aristoflex® AVC, the copolymers being identified by respective INCI nomenclature of Sodium Acrylate/Sodium Acryloyldimethyl Taurate and Acryloyl Dimethyltaurate/Vinyl Pyrrolidone Copolymer.

Amounts of the thickener may range from about 0.001 to about 5%, preferably from about 0.1 to about 2%, optimally from about 0.2 to about 0.5% by weight.

Fragrances and abrasives may also be included in compositions of the present invention. Each of these substances may range from about 0.05 to about 5%, preferably between 0.1 and 3% by weight.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The following Examples will more fully illustrate the embodiments of this invention. All parts, percentages and proportions referred to herein and in the appended claims are by weight unless otherwise indicated.

EXAMPLE 1

A series of lotions according to the present invention are reported in the Table below.

TABLE I

| Component | Sample (Weight %) | | | | | |
|---|---|---|---|---|---|---|
| | A | B | C | D | E | F |
| Stearic Acid | 2.40 | 2.40 | 3.00 | 3.00 | 1.95 | 1.95 |
| Glyceryl Monostearate/Stearamide AMP | 1.40 | 1.50 | 1.50 | 1.05 | 1.05 | 3.10 |
| Glycerol Monostearate | 0.65 | 0.65 | 0.65 | 0.65 | 0.65 | 0.65 |
| Cetyl Alcohol | 0.37 | 0.37 | 0.37 | 0.37 | 0.37 | 0.37 |
| Petrolatum | 1.25 | 1.25 | 3.59 | 0.80 | 3.80 | 4.35 |
| Isopropylmyristate | 1.30 | 1.30 | 1.30 | 1.30 | 1.30 | 1.30 |
| Disodium EDTA | 0.05 | 0.05 | 0.05 | 0.05 | 0.05 | 0.05 |
| Induchem Beads* | 2.00 | 1.00 | 4.00 | 4.00 | 8.00 | 8.00 |
| Glycerin | 10.00 | 10.00 | 5.00 | 5.00 | 5.00 | 10.00 |
| Simulgel EG ® | 0.75 | 0.75 | 0.75 | 0.75 | 0.75 | 0.75 |
| Titanium Dioxide | 0.10 | 0.20 | 0.80 | 0.10 | 0.20 | 0.10 |
| Triethanolamine (99%) | 0.70 | 0.70 | 0.90 | 0.90 | 0.60 | 0.60 |
| Glydant Plus ® | 0.09 | 0.09 | 0.09 | 0.09 | 0.09 | 0.09 |
| DMDM Hydantoin | 0.17 | 0.17 | 0.17 | 0.17 | 0.17 | 0.17 |
| Silicone 50 ct | 1.50 | 1.50 | 1.50 | 1.50 | 1.50 | 1.50 |
| Silicone DC 1501 ® | 0.50 | 0.50 | 0.50 | 0.50 | 0.50 | 0.50 |
| Dihydroxyacetone | 1.00 | 1.50 | 2.50 | 2.50 | 1.00 | 4.50 |
| Fragrance | 0.30 | 0.30 | 0.30 | 030 | 0.30 | 0.30 |
| Water | Balance | Balance | Balance | Balance | Balance | Balance |

*Beads are provided with a mixture of iron oxides replicating a tan color.

The samples of Table 1 are formulated in the following manner. A reactor is charged with the deionized water and disodium EDTA. Heat is applied till 60° C. in combination with stirred mixing. The Induchem beads are added and heating continued for 10 minutes. Simulgel EG® is added to the reactor and the temperature maintained at 77-80° C. for 10 to 15 minutes. In a separate vessel, the oil phase components are added. Light mixing of the batch is performed with heating in a water bath to 75-77° C. The water reactor is maintained at 60-65° C. and slow addition occurred for glycerin, titanium dioxide and triethanolamine. Continuous mixing is done until the aqueous system is uniform. Very slowly the oil phase is added to the water phase at 75-77° C. under moderate mixing. After full emulsification, the batch is agitated for a further 5 minutes. Thereupon the resultant emulsion is homogenized using an ARDE Barenco® apparatus for 20-30 seconds at 35%. The resultant system is then topped with further deionized water. Cooling is then begun with a large sweep) (50 rpm) mixer. Preservatives Glydant Plus® and DMDM Hydantoin are then added with the batch held at 50-55° C. Thereafter a slurry of dihydroxyacetone in the silicone oils is added to the batch. At a temperature of 45-50° C., the fragrance is charged to the reactor. Heating is then discontinued and mixing stopped when the temperature reaches 38-40° C.

EXAMPLE 2

Experiments were conducted to demonstrate performance of compositions according to the present invention. A base formula was prepared as outlined in Table II.

TABLE II

| Component | Base Formula (Weight %) |
|---|---|
| Stearic Acid | 2.40 |
| Glyceryl Monostearate/Stearamide AMP | 1.40 |
| Glycerol Monostearate | 0.65 |
| Cetyl Alcohol | 0.37 |
| Petrolatum | 1.25 |
| Isopropylmyristate | 1.30 |
| Disodium EDTA | 0.05 |
| Glycerin | 10.00 |
| Simulgel EG ® | 0.75 |
| Titanium Dioxide | 0.10 |
| Triethanolamine (99%) | 0.70 |
| Glydant Plus ® | 0.09 |
| DMDM Hydantoin | 0.17 |
| Silicone 50 ct | 1.50 |
| Silicone DC 1501 ® | 0.50 |
| Fragrance | 0.30 |
| Water | Balance |

Three compositions were prepared by combining dihydroxyacetone and Unisphere beads (provided by Induchem USA, Inc.) in differing amounts. Sample A was the base formula also containing 6% dihydroxyacetone (DHA), but beads were absent. Sample B was the base formula with 6% DHA and 6% Induchem beads by weight of the overall composition. The Induchem beads contained mannitol (25-50%), cellulose (15-20%), hydroxypropyl cellulose (less than 1%), tbtan;um dioxide (10-15%) and iron oxide (5-10%). Final loading of pigment (tianium dioxide and iron oxides was approximately 40% by weight of the beads). These beads were surrounded by an outer coating of acrylate polymer (1-5%), a nonionic alkoxylated dilspersant (5-10%) and titanium dioxide (2-10%). The resultant beads were visually white. Sample C was the base formula with 6% Induchem beads but without any DHA. Results are recorded in Table III. The greater the negative value, the better the tanning performance.

TABLE III

| Sample | Actives | \multicolumn{5}{c}{Time (Hours)*} |
|---|---|---|---|---|---|---|
| | | 1 | 2 | 3 | 22 | 29 |
| A | DHA | 0.5 | −0.5 | −2.5 | −6.2 | −5.8 |
| B | DHA/Beads | −1.2 | −4.2 | −5.8 | −7.8 | −8.5 |
| C | Beads | 0.5 | 0.5 | 0.7 | 0.7 | 0.6 |

*Values in the table represent the change (delta) in L-a*-b*

Tanning measurements were done with a CM-2500 C spectrophotometer to measure the L* and b* values. The minimal perceivable tanning effect is around −2. Values in Table III are the calculation of L*−b* from the spectrophotometric measurement.

Each of the samples were applied to the forearm of panelists. Rubbing-in time was 2 minutes. Spectrophotometric measurements were then taken at times 0, 1, 2, 3, 22 and 29 hours.

Table III reveals that the beads alone (Sample C) provided no significant darkening effect on skin. Sample A with only DHA provided an expected amount of tan. The surprising result was with Sample B. Here the combination of DHA and beads gave initial darkening faster but also provided a longer lasting darkening effect.

What is claimed is:

1. A cosmetic composition comprising:
   (i) from about 0.05 to about 15% by weight of the composition of a sunless tanning agent;
   (ii) from about 0.1 to about 20% by weight of the composition of beads formed of a cellulose or a cellulose derivative having an average particle size ranging from about 100 to about 3,000 micron;
   (iii) from about 1 to about 60% by weight of the beads of a water-insoluble pigment incorporated within a matrix of the beads, the pigment comprising an iron oxide mixture having a tan color;
   (iv) from about 0.1 to about 10% by weight of the beads of a colorant held within a coating surrounding the matrix, the coating having a color other than tan, the coating comprising 1 to 5% by weight of acrylate polymer, 5 to 10% by weight of nonionic alkoxylated dispersant and 2 to 10% by weight of titanium dioxide; and
   (v) a cosmetically acceptable carrier.

2. The composition according to claim 1 wherein the sunless tanning agent is dihydroxyacetone.

3. The composition according to claim 1 wherein the sunless tanning agent is a combination of dihydroxyacetone and erythrulose in a relative weight ratio of 6:1 to 1:2.

4. The composition according to claim 3 wherein the ratio is 4:1 to 2:1.

5. The composition according to claim 1 wherein the beads have a matrix formed from mannitol, cellulose and hydroxypropyl methylcellulose.

6. A method for sunless tanning or providing a glow/shine to skin comprising:
   (A) providing a cosmetic composition comprising:
      (i) from about 0.05 to about 15% by weight of the composition of a sunless tanning agent;
      (ii) from about 0.1 to about 20% by weight of the composition of beads formed of a cellulose or a cellulose derivative having an average particle size ranging from about 100 to about 3,000 micron (μm);
      (iii) from about 1 to about 60% by weight of the beads of a water-insoluble pigment comprising an iron oxide mixture incorporated within a matrix of the beads, the pigment having a tan color;
      (iv) from about 0.1 to about 10% by weight of the beads of a colorant held within a coating surrounding the matrix, the coating having a color other than tan, the coating comprising 1 to 5% by weight of acrylate polymer, 5 to 10% by weight of nonionic alkoxylated dispersant and 2 to 10% by weight of titanium dioxide;
      (v) a cosmetically acceptable carrier; and
   (B) applying the cosmetic composition to the skin.

* * * * *